United States Patent
Grönberg

(10) Patent No.: US 9,289,214 B2
(45) Date of Patent: Mar. 22, 2016

(54) MOUNTING TOOL FOR ANASTOMOSIS DEVICE

(75) Inventor: Anders Grönberg, Halmstad (SE)

(73) Assignee: CARPONOVUM AB, Lund (SE)

( * ) Notice: Subject to any disclaimer, the term of this patent is extended or adjusted under 35 U.S.C. 154(b) by 477 days.

(21) Appl. No.: 13/258,076

(22) PCT Filed: Mar. 18, 2010

(86) PCT No.: PCT/EP2010/053525
§ 371 (c)(1),
(2), (4) Date: Oct. 28, 2011

(87) PCT Pub. No.: WO2010/108844
PCT Pub. Date: Sep. 30, 2010

(65) Prior Publication Data
US 2012/0071906 A1  Mar. 22, 2012

Related U.S. Application Data

(60) Provisional application No. 61/163,420, filed on Mar. 25, 2009.

(30) Foreign Application Priority Data

Mar. 25, 2009  (SE) ...................................... 0950189

(51) Int. Cl.
A61B 17/10  (2006.01)
A61B 17/11  (2006.01)

(52) U.S. Cl.
CPC ..... A61B 17/1114 (2013.01); A61B 2017/1132 (2013.01)

(58) Field of Classification Search
CPC ................... A61B 17/1114; A61B 2017/1132; A61B 17/11; A61B 17/115; A61B 17/1155; A61B 2017/07257; A61B 2017/07264; A61B 2017/1103; A61B 2017/1107; A61B 2017/111; A61B 2017/1114; A61B 2017/1121; A61B 2017/1135; A61B 2017/1139; A61B 2017/1157; A61F 2/064
USPC .................................................. 606/140, 153
See application file for complete search history.

(56) References Cited

U.S. PATENT DOCUMENTS 4,567,891 A * 2/1986 Kanshin et al. ............... 606/153
4,964,863 A * 10/1990 Kanshin et al. ............... 606/153
(Continued)

FOREIGN PATENT DOCUMENTS

JP  2005-533624  11/2005
WO  2004008936 A2  1/2004
(Continued)

Primary Examiner — David C Eastwood
Assistant Examiner — Martin T Ton
(74) Attorney, Agent, or Firm — Capitol City TechLaw

(57) ABSTRACT

A mounting tool for mounting a flexible ring-shaped part of an anastomotic device on a rigid part of an anstomotic device is provided. The tool comprises a receiving portion (104) in a distal end of the mounting tool for receiving the flexible part thereat and a handle portion (103) proximally of said receiving portion (104). Said receiving portion (104) comprises an elongated tubular sheet element (101), and a tubular displacement element (201), arranged within the sheet element (101) to be longitudinally displaceable in relation to the sheet element (101), such that a shelf (401) is obtained circumferentially of the tubular displacement element (106) and distally of the sheet element (101). The shelf (401) is configured to receive the flexible part. A mounting tool for receiving a flexible ring-shaped part of an anastomotic device on a rigid part of an anstomotic device is also provided. This tool comprises a longitudinal guiding element (801) for passing through a central passage or lumen in a mounting tool according to above, and a connection plate (802) arranged distally on the guiding element (801). The connection plate (802) is configured to connect to a rigid part of an anstomotic device. A kit is also provided.

20 Claims, 12 Drawing Sheets

(56) References Cited

U.S. PATENT DOCUMENTS

| | | | |
|---|---|---|---|
| 5,346,501 A * | 9/1994 | Regula et al. | 606/151 |
| 5,423,330 A * | 6/1995 | Lee | 600/566 |
| 6,117,148 A | 9/2000 | Ravo et al. | |
| 8,205,782 B2 * | 6/2012 | Harari et al. | 227/180.1 |
| 2002/0091397 A1 * | 7/2002 | Chen | 606/153 |
| 2004/0015179 A1 | 1/2004 | Monassevitch et al. | |
| 2005/0021085 A1 | 1/2005 | Abrams et al. | |
| 2005/0137614 A1 * | 6/2005 | Porter et al. | 606/153 |
| 2006/0085035 A1 * | 4/2006 | Viola | 606/219 |

FOREIGN PATENT DOCUMENTS

| | | |
|---|---|---|
| WO | 2004008937 A2 | 1/2004 |
| WO | 2007122220 A2 | 11/2007 |
| WO | 2007122223 A1 | 11/2007 |

* cited by examiner

MOUNTING TOOL FOR ANASTOMOSIS DEVICE

CROSS REFERENCE TO RELATED APPLICATIONS

This application claims the benefit under 35 USC 119(e) to U.S. Provisional Patent Application No. 61/163,420 filed on Mar. 25, 2009.

FIELD OF THE INVENTION

This invention pertains in general to the field of a mounting tool for assembling an anastomotic device, comprising a rigid part and a flexible part of generally hollow open configuration, to an end of a tubular structure. More particularly, the invention pertains to a mounting tool for mounting such an anastomotic device, said mounting tool comprising a first part having a portion for receiving the rigid part of the anastomotic device, and a second part for receiving the flexible part of the anastomotic device, said first and second part being cooperative to arrange the flexible part circumferentially of the rigid part.

BACKGROUND OF THE INVENTION

Colorectal cancer is the third most frequent type of cancer in the world, having an occurrence of about 1 million new cases every year. The incidents of cancer are considerably more frequent in the industrial part of the world.

Current techniques for mechanically performing anastomosis of hollow organs use circular mechanical staplers, which execute the connection of the tissue edges of the dissected hollow organ by metallic or plastic staples. A wide variety of surgical staplers have been developed for gastric, oesophageal and intestinal surgery. In performing surgical anastomotic stapling, generally two pieces of the hollow organ are joined by a ring of staples with a closed loopstapler. End to end anastomoses are generally performed by intraluminal surgical staplers that deliver a pair of staggered rings of staples. During this process, a circular knife blade is used to separate the tissue that is held within the circular ring. The separated tissue is then removed with the stapler to form a circular opening within the lumen along the stapling line.

A major issue regarding anastomosis healing is the blood circulation of the anastomosis during the healing process. Despite substantial development of surgical techniques during the last decades, morbidity and mortality after resections in the gastrointestinal tract, e.g. due to anastomotic leakage, remain as serious problems. Ischemia and inflammation, which are natural parts of the healing process, may cause leakage and secondary infection that may be fatal for the patient in the stapling area. Therefore, it has become common practice to relieve the pressure from the anastomosis by performing a deviating stoma, especially when the anastomosis is carried out in the lower part of colon and in rectum. By relieving pressure and faecal stream from the anastomosis during the healing process, the leakage incident may be reduced and fatal consequences of anastomotic dehiscence can be avoided. The inconvenience for the patient is obvious, since the patient must have a temporary stoma for a time period of about 3-6 months, and then has to undergo a second surgery in order to close the stoma. Unfortunately in many cases, the closure of the stoma cannot be reversed and the patient is forced to live with a permanent stoma leading to lower quality of life associated with increased costs. Another problem arising from stapling of anastomoses is anastomotic stenosis. The critical area for healing is the contact area between the two ends of the hollow structure to be connected. The connection has to be liquid proof, and the cross section of the lumen should be as wide and flexible as the original lumen. The size of the stapler determines the size of the lumen and thus the contact area between the ends. Surgical staplers create a smaller and more rigid opening compared to the cross section of the original lumen due to the staples inside the hollow structure connecting the two ends thereof, i.e. a collar may be formed that may lead to stenosis. For solving this problem repeated need for dilatation is required.

In this regard WO 2007/122223 discloses an anastomotic device for anastomosis of a tubular structure, such as an intestine, said device comprising members of a generally hollow open configuration. The device comprises a first member and a second member, wherein the first and second member each comprises a rigid part and an elastic part, respectively, and a connection member for connecting the first and second members to each other. This device improves the anastomosis by minimizing stenosis, while providing a self-discarding system.

WO 2007/122220 discloses a mounting tool for mounting such an anastomotic device to an end of an intestine. The mounting tool hereof comprises a receiving portion for receiving a rigid part of said device and a conical portion with a large end facing said rigid part having a diameter larger than or equal to the rigid part and a small end. The conical portion is insertable into the elastic part already arranged inside the tubular structure for expanding the diameter thereof and for passing the elastic part beyond the large end and onto a rigid part arrange able at the receiving portion.

However, when tumours are removed from lower part of the large intestine i.e. rectum, these parts of the intestinal system are inaccessible from the abdominal cavity. The pelvis minor is very narrow and funnel shaped, making it almost impossible to perform an anstomose from insert a hand from above. This fact severely hampers the possibility for working and suturing the area. In the last part of rectum, i.e. the bottom of the funnel and 5 to 10 cm from the sphincter, there is no possibility to reach from the abdominal cavity.

Hence, an improved mounting system would be advantageous and in particular a mounting system allowing for increased flexibility, cost-effectiveness, providing improved access to the lower part of the large intestine, rectum, and anal and/or improved control of the flexible part inside the intestine would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a mounting tool for mounting a flexible ring-shaped part of an anastomotic device on a rigid part of an anstomotic device, said tool comprising: a receiving portion in a distal end of the mounting tool for receiving the flexible part thereat; a handle portion proximally of said receiving portion; characterized in that said receiving portion comprises an elongated tubular sheet element, and a tubular displacement element, arranged within the sheet element to be longitudinally displaceable in relation to the sheet element, such that a shelf is obtained circumferentially of the tubular displacement element and distally of the sheet element, said shelf being configured to receive the flexible part; and a mounting tool for receiving a flexible ring-shaped part of an anastomotic device on a rigid part of an anstomotic device, said tool comprising: a longitudinal guiding element for passing through a central passage or lumen in a mounting tool for mounting a flexible ring-shaped part of an anastomotic device on a rigid part of an anstomotic device; and a connection plate arranged distally on the guiding element, said connection plate being configured to connect to a rigid part of an anstomotic device.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Figure 1:
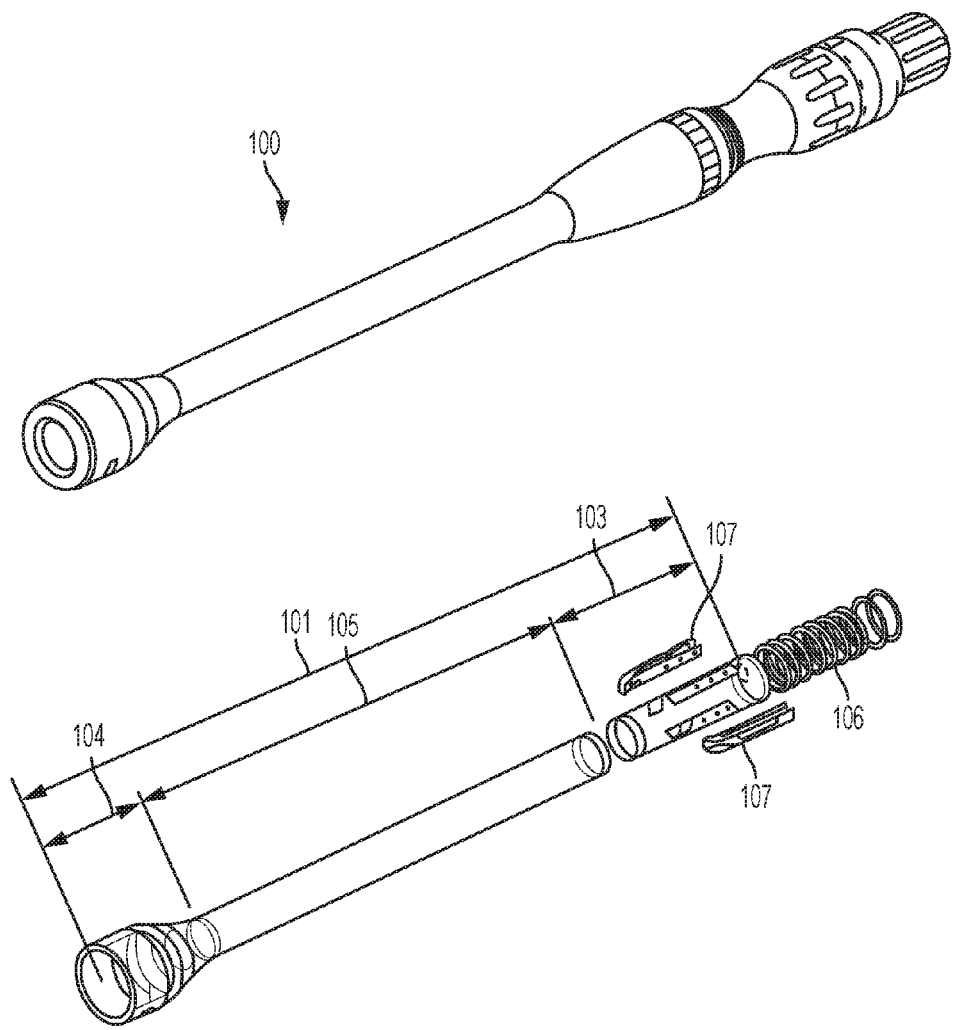
FIG. 1 illustrates an embodiment of a sheet element of a mounting tool according to the present invention.

The following description focuses on a mounting tool for assembling an anastomotic device, said anastomotic device comprising a rigid part and a flexible part of generally hollow open configuration, to an end of an intestine. Such anastomotic device is disclosed in the international patent application with publication number WO 2007/122223. More particularly, such an anastomotic device comprises a first and a second member of generally hollow open configurations, wherein the first and second member each comprises a rigid part and an elastic part, respectively. The anastomotic device further comprises a connection member for connecting the first and second members to each other. Each elastic part thereof are configured to be arranged circumferentially of each rigid part, respectively, such that anastomosis is obtained, in use, at a contact area in-between the elastic parts. As disclosed in WO 2007/122223, said rigid parts are connected by configuring one of the rigid parts with a male connecting part and the other with a female connecting part. Each end of an incisioned intestine is connected to the rigid parts, respectively, by clamping each end of the intestine between a rigid and a flexible part. Such end of an intestine is obtained after removing, such as by incision, a part of the intestine. More particularly, the invention pertains to a mounting tool for mounting such an anastomotic device, said mounting tool comprising a first part having a portion for receiving the rigid part of the anastomotic device, and a second part for receiving the flexible part of the anastomotic device, said first and second part being cooperative to arrange the flexible part circumferentially of the rigid part. However, it will be appreciated that the invention is not limited to this application but may be applied to many other technical fields, including for example the arrangement of such anastomotic devices on other tubular structures.

According to a first embodiment, the mounting tool comprises a first part 100. The first part 100 comprises an elongated tubular sheet element 101, according to FIG. 1. In the proximal end of the first part a handle portion 103 is arranged. In the distal end of the first part 100 a receiving portion 104 for receiving a flexible part of an anastomotic device thereat is arranged. The handle portion 103 and the receiving portion 104 are connected via a central portion 105. The central portion 105 may have an outer diameter in the cross-section in the transversal plane that is smaller than the cross-section in the transversal plane of the handle portion 103 and/or the receiving portion 104. The first part 100 is to be inserted through the sphincter of a patient undergoing anastomosis of intestine. Once the receiving portion 104 of the first part 100 has been inserted, the central part 105 is to be situated adjacent the sphincter of the patient. The smaller diameter of the central part reduces the stress on the sphincter.

Figure 2:
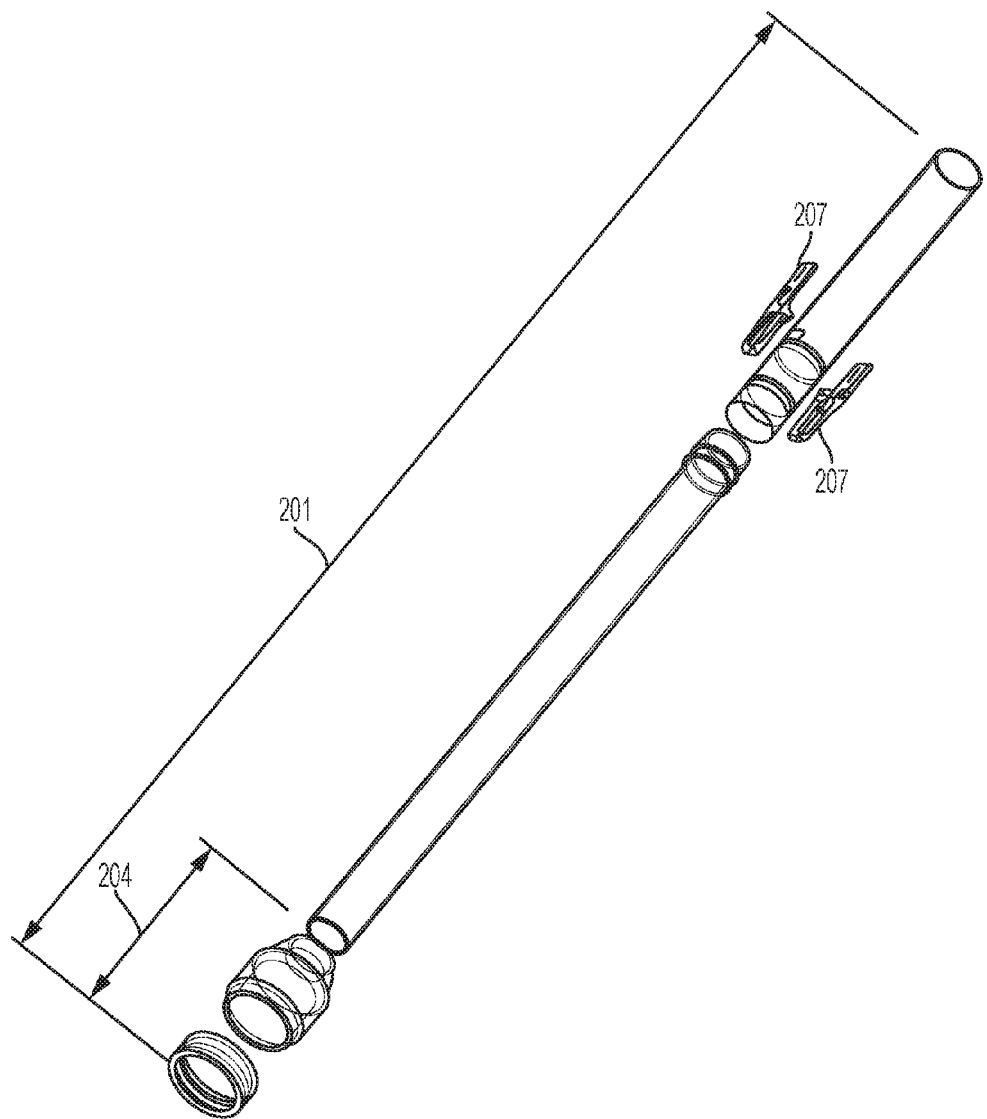
FIG. 2 illustrates an embodiment of a displacement element of a mounting tool according to the present invention.

Within the sheet element 101 a tubular displacement element 201 may be arranged, in accordance with FIG. 2. The handle portion 103 may be an integral part of, or connected to, the displacement element 201 in the proximal end of the displacement element 201. In the distal end of the displacement element 201 a distal part 204 is located within the receiving portion 104 of the sheet element 101. The distal part 204 is configured to have an outer diameter corresponding to the inner diameter of the distal end of the sheet element 101. The tubular displacement element 201 is arranged to be longitudinally displaceable within the elongated tubular sheet element 101, relative the elongated tubular sheet element 101. In this respect the elongated tubular sheet element 101 and the tubular displacement element 201 may have ring-shaped cross sections in the transversal plane, where an outer diameter of the tubular displacement element 201 substantially corresponds to the inner diameter of the elongated tubular sheet element 101, such that the tubular displacement element 201 may run longitudinally inside the elongated tubular sheet element 101.

Figure 3:
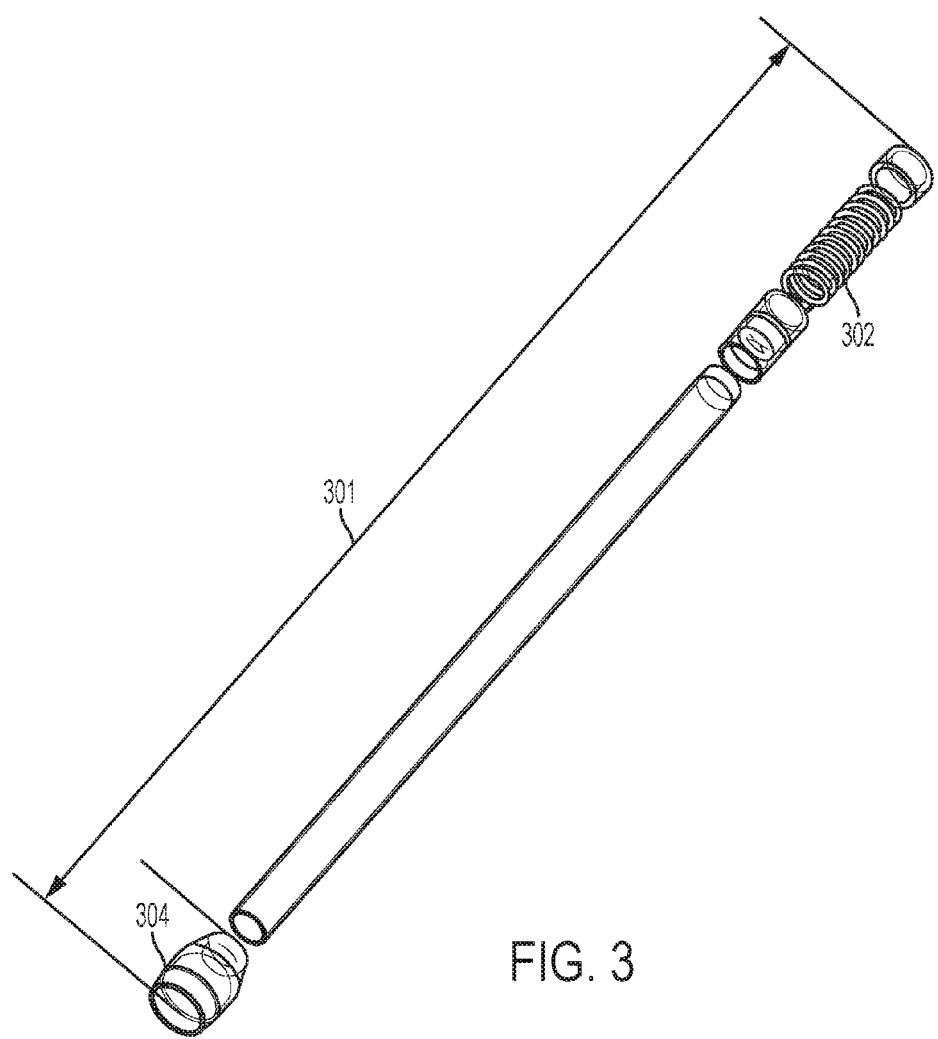
FIG. 3 illustrates an embodiment of an elongated tubular cutting element of a mounting tool according to the present invention.

Inside the tubular displacement element 201 and the elongated tubular sheet element 101 an elongated tubular cutting element 301 may be arranged, in accordance with FIG. 3. The tubular cutting element 301 is then arranged to be longitudinally displaceable within and in relation to the elongated tubular sheet element 101 and/or the tubular displacement element 201. In the distal end of the cutting element 301 a distal part 304 is located within the distal part 204 of the displacement element 201 inside the receiving portion 104 of the sheet element 101. The distal part 304 is configured to have an outer diameter corresponding to the inner diameter of the distal end of the sheet element 101, while simultaneously having a cutting edge in the very distal end of the cutting element 301. Thus, in the very distal end of the tubular cutting element 301 a knife element may be arranged. The knife element may be integrated with the central part of the cutting element 301, such that the distal end of the cutting element 301 is chamfered/sharpened into a sharp edge to thereby form the knife element. The cutting element 301 may then be longitudinally and distally displaced from a non-cutting position into a cutting position. Also the tubular cutting element 301 may have ring-shaped cross sections in the transversal plane, where an outer diameter of the tubular cutting element 301 substantially corresponds to the inner diameter of the elongated tubular displacement element 201, such that the tubular cutting element 301 may run longitudinally inside the elongated tubular displacement element 201.

Figure 4:
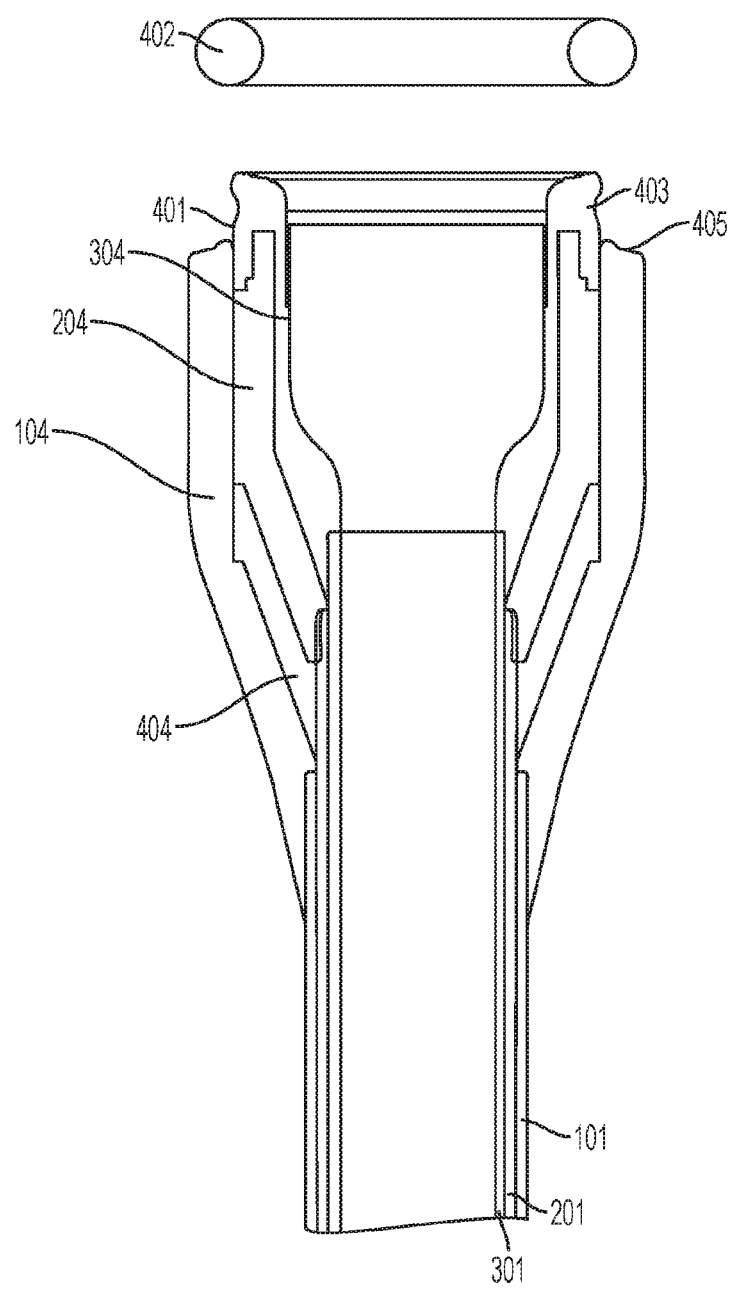
FIG. 4 illustrates a cross section of a receiving portion of an embodiment of a mounting tool according to the present invention.

In a first state the tubular displacement element 201 may extend distally of the elongated tubular sheet element 101, such that a receiving shelf 401 is obtained circumferentially of the tubular displacement element 201 and distally of the tubular sheet element 101, in accordance with FIG. 4. FIG. 4 discloses a cross section of the receiving portion 104. The shelf 401 is configured to receive a flexible part 402 of an anastomotic device, according to above, thereon. The distal part 204 of the displacement element 201 may have an annular recess 403, adapted to house a flexible part 402 of an anastomotic device. With the recess 403, the flexible part 402 of the anastomotic device will have improved seating on the displacement element 201. Thus, the shelf 401 may be preloaded with a flexible part 402 of an anastomotic device, before insertion of the first part 100 through the sphincter of the patient. By displacing the elongated tubular sheet element 101 distally in relation to the tubular displacement element 201 into a second state, a flexible part 402 of an anastomotic device arranged on the receiving shelf 401, may be pushed off the shelf 401, which will be further elucidated below. To enable the displacement of the elongated tubular sheet element 101 distally in relation to the tubular displacement element 201, in the case where the diameter of the receiving portion 104 has a larger diameter than the central portion 105, there may be a 404 void in-between the tubular sheet element 101 and tubular displacement element 201, in the proximal end of the receiving portion 104. Thus, the void 404 is configured to allow distal and proximal displacement between the tubular sheet element 101 and tubular displacement element 201. The displacement stops once the void has been eliminated, such that the tubular sheet element 101 and tubular displacement element 201 interacts in the proximal end of the receiving portion 104. The distal end of the sheet element 101 may be chamfered or cup-shaped, such that the chamfer face or cup-shaped face 405 will face outwardly from the first part 100. Thus, when the flexible part 402 of an anastomotic device arranged on the receiving shelf 401 is pushed off the shelf 401, the chamfer or cup-shape 405 will push the flexible part 402 radially outwards while simultaneously pushing the flexible part 402 distally off the shelf 401. This ensures an improved transportation of the flexible part 402 onto a rigid part of an anastomotic device located distally of the first part 100.

Proximally of the receiving portion 104, such as in the proximal ends of the tubular sheet element 101 and the tubular cutting element 301, said tubular sheet element 101 and cutting element 301 may be spring loaded. The tubular sheet element 101 may be spring loaded with a spring 106 such that a release of the spring load will move the sheet element 101 distally in relation to the displacement element 201.

Alternatively, the displacement element 201 may be spring loaded such that a release of the spring load will move the displacement element 201 proximally in relation to the sheet element 101. In this embodiment, the handle portion 103 may be attached to the sheet element 101. Thus, the cutting element 301 will move proximally together with the displacement element 201. The cutting element 301 may be spring loaded with a spring 302, such that a release of the spring load will move the cutting element 301 distally in relation to the sheet element 101 and/or the displacement element 201. This action may be performed after the displacement element 201 previously has been moved proximally together with the cutting element 301.

Thus, the sheet element 101, the displacement element 201, and the cutting element 301 may be individually spring loaded, such that they may be individually displaced proximally and distally, respectively, along the longitudinal direction of the first part 100, when the spring loads, respectively, are released. The release of the spring load may be accomplished by pushing a first set of release bars 107 and a second set of release bars 207, corresponding to movement of the sheet element 101 or the displacement element 201, and the cutting element 301, respectively.

According to the embodiment of FIGS. 1 and 2, the release of the spring load may be accomplished by pushing a first set of release bars 107 and a second set of release bars 207, corresponding to the sheet element 101 and the cutting element 301, respectively, even though it is possible to reverse the arrangement of the first set of release bars 107, described below, to obtain a proximal movement of the displacement element 201 in relation to the sheet element 101.

Figure 5:
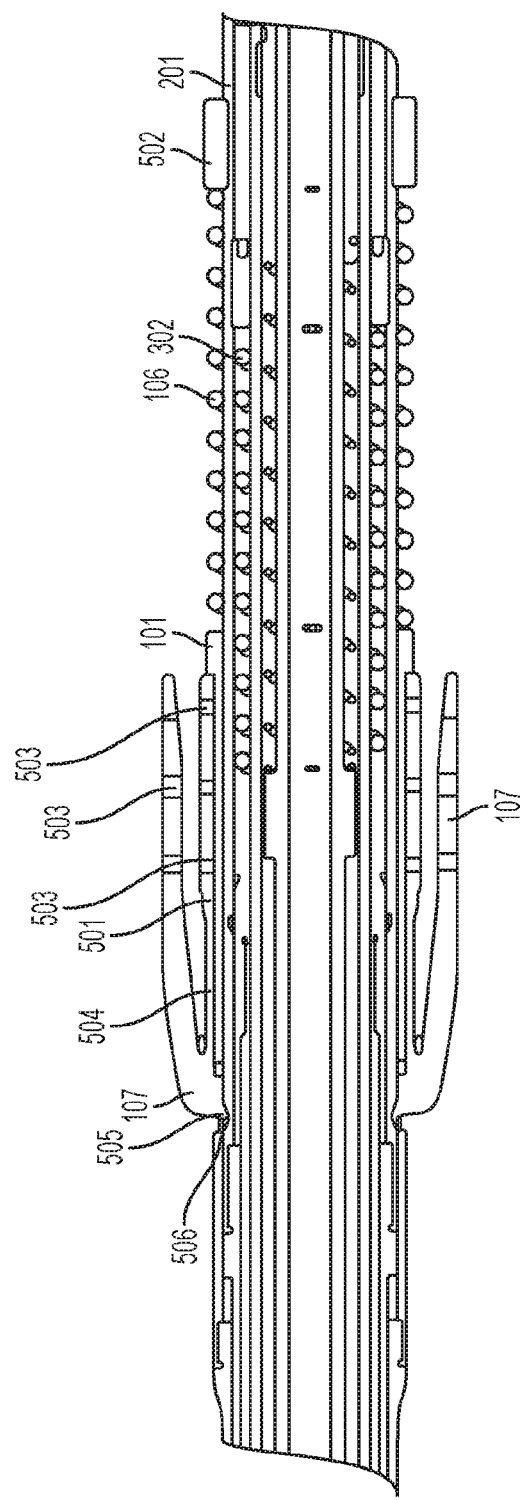
FIG. 5 illustrates a cross section of a spring arrangement in the y-z plane of an embodiment of a mounting tool according to the present invention.
Figure 6:
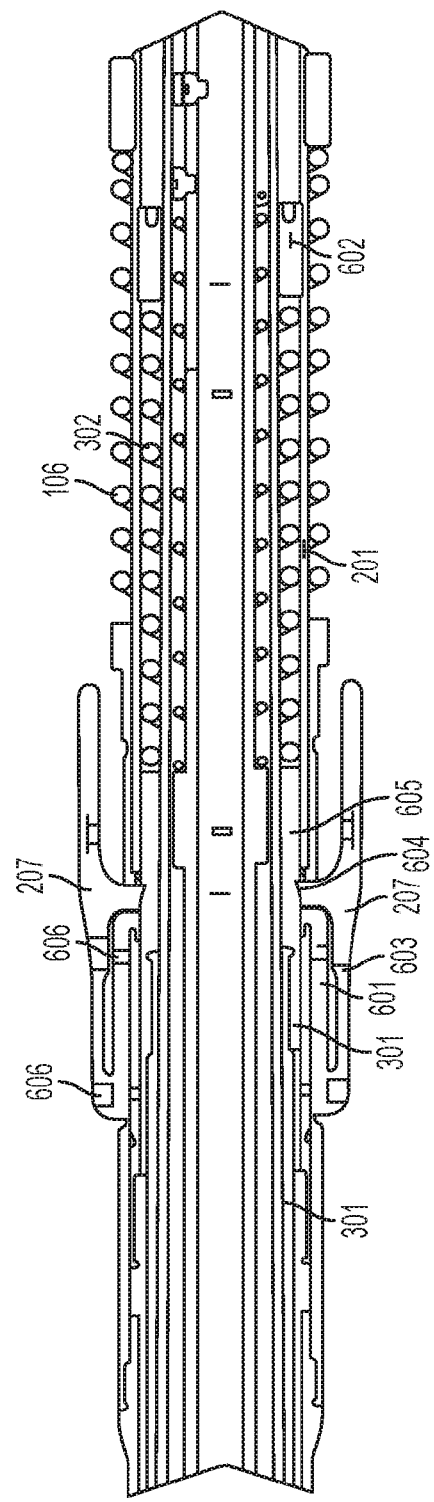
FIG. 6 illustrates a cross section of a spring arrangement in the x-z plane of an embodiment of a mounting tool according to the present invention.

FIGS. 5 and 6 illustrate cross sections of the spring arrangement for an embodiment, wherein a set of first release bars 107 and a set of second release bars 207 correspond to the sheet element 101 and the cutting element 301, respectively.

FIG. 5 illustrates the first set of release bars 107 in a cross section in the y-z plane. The release bars 107 have a supporting ridge 501. A spring load washer 502, locked to the tubular displacement element 201, is arranged proximally of the spring 106, such that the spring 106 is arranged in between the spring load washer 502 and the sheet element 101. Alternatively, the spring load washer may be integrated with the tubular displacement element 201. In the distal end, the first release bars 107 are connected to the sheet element 101 by screws 503. The distal end the supporting ridge 501 is provided with an inwardly directed flange 505. In a spring loaded position the flange 505 engages a notch 506 in the underlying tubular element, such as the displacement element 201. When a proximal part of the first release bar 107, i.e. the free end, is pushed inwardly—towards the central axis of the first part 100—the supporting ridge 501 will transfer the pushing force by lever to lift the tongue 504 and the flange 505. The flange 505 is then lifted to disengage the notch in the underlying tubular element, such as the displacement element 201. This will release the spring load, transferring the load into movement of the sheet element 101 in a longitudinal distal direction, such that the sheet element 101 is in a released position. When two first release bars 107 are used, it can be assured that the sheet element not is released until both first release bars 107 are pushed inwardly.

FIG. 6 illustrates the second set of release bars 207 in cross section in the x-z plane. The release bars 207 have a supporting ridge 601. The supporting ridge 601 may be connected to the tubular displacement element 201 with screws 606. A spring load washer 602 may be arranged proximally of the spring 302. The spring load washer may be locked to or integrated with the tubular displacement element 201 or the cutting element 301. The spring load washer 602 may also be threadingly mated with the tubular displacement element 201 or the cutting element 301, such that it may increase or decrease the spring tension. The release bars 207 are connected to the supporting ridge 601 by a tongue 603. The proximal end of the tongue 603 is provided with an inwardly directed flange 604. In a spring loaded position the flange 604 engages a notch 605 in the underlying cutting element 301. The proximal end of the second set of release bars 207 extends radially outward from the part of the second release bar 207 connected to the tongue 603, whereby free proximal ends of the second release bars 207 are obtained. Thus, when the proximal part of the second release bar 207, i.e. the free end, is pulled outwardly—out from the central axis of the first part 100—the supporting ridge 601 will transfer the pulling force by lever to lift the tongue 603 and the flange 604. The flange 604 is then lifted to disengage the notch 605 in the underlying cutting element 301. This will release the spring load, transferring the load into movement of the cutting element 301 in a longitudinal distal direction. When two second release bars 302 are used, it can be assured that the sheet element not is released until both second release bars 302 are pulled outwardly.

Within the elongated tubular sheet element 101, the tubular displacement element 201, and the tubular cutting element 301, a central passage or lumen is formed. This central passage may be connected to a suction device in the proximal end of the first part 100.

In one embodiment, a protective element may be arranged in the distal end of the first part 100. The protective element may be an inflatable disc, configured to be positioned distally and radially outwards from the shelf 401, such that a flexible part of the anastomotic device positioned on the shelf 401 may be maintained on the shelf 401 during insertion of the first part 100 through the sphincter of the patient. The inflatable disc may be attached to a longitudinal hollow element, which is configured to be positioned in the central passage during insertion. The inflatable disc may then be connected to a blowing means proximally of the handle portion, whereby the pressure in the inflatable disc may be maintained high enough to preserve the effect of protecting the flexible part of the anastomotic device from falling off. Alternatively, the pressure may be prepared high enough in the inflatable disc by a valve member in the handle portion of the first part 100. After insertion of the first part 100 through the sphincter, the inflatable disc may be deflated/evacuated, whereafter the longitudinal hollow element together with the inflatable disc may be pulled proximally through the central passage, to liberate the flexible part of the anastomotic device positioned on the shelf 401. In one embodiment the protective element is a flexible cushion element, configured to be pulled proximally through the central passage after insertion of the first part 100.

Figure 7:
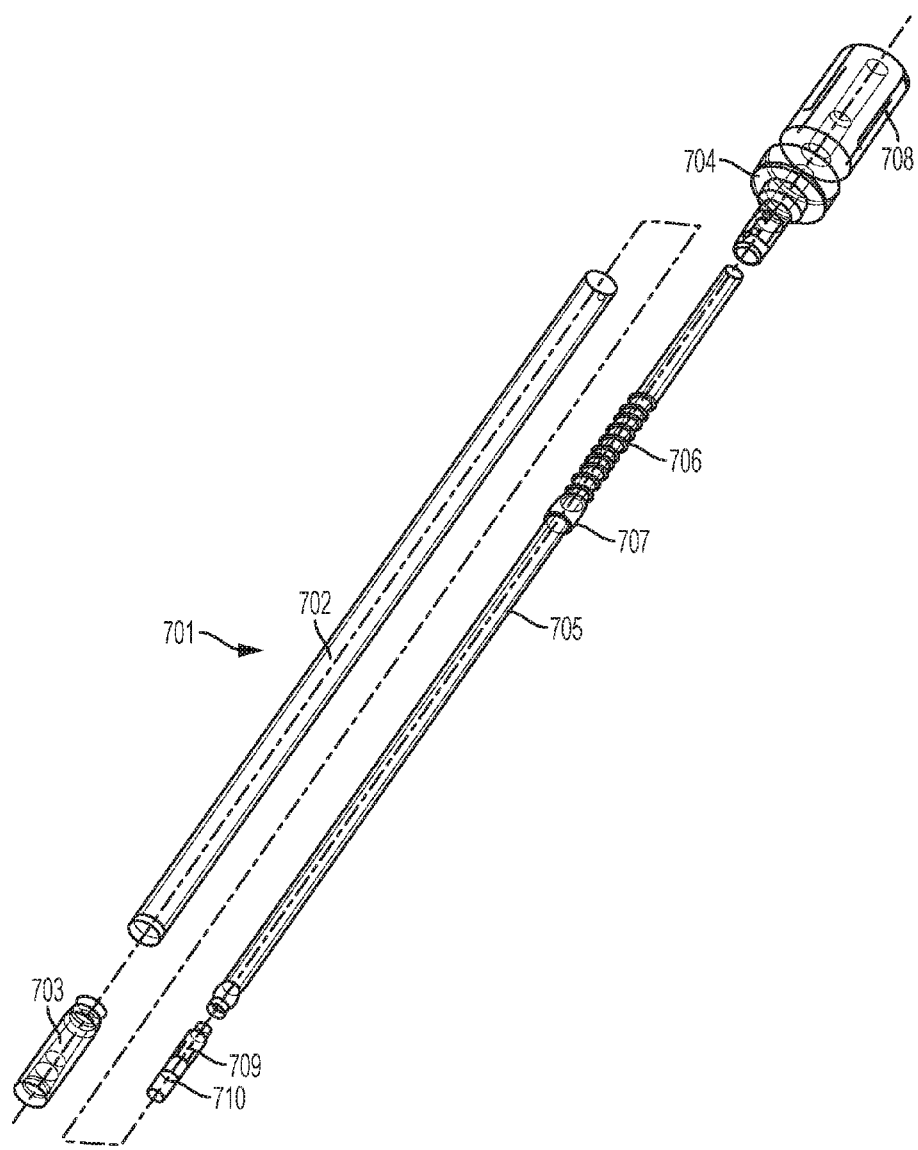
FIG. 7 illustrates an embodiment of a fixation element of a mounting tool according to the present invention.

In the central passage or lumen, a tubular fixation element 701, in accordance with FIG. 7, may be arranged. The fixation element 701 comprises a tubular connector element 702. In the distal end of the tubular connector element 702 a top connector 703 is arranged. The top connector 703 is a tubular element. The inner diameter of the top connector 703 increases in the proximal-distal direction. In this respect, the inner diameter is d1 in the distal end and d2 in the proximal end, where d1 is greater than d2. The connector element 702 may have a central transformation zone for transition from d1 to d2. In the proximal end of the connector element 702, the connector element 702 is attached, such as by threads, to a connector unit 704. The displacement element 201 may also be connected to the connector unit 704, such as by threads. Inside the connector element 702 a tubular locking element 705 may be arranged. The connector unit 704 may run on the locking element 705, while being attached thereto by a spring mechanism, comprising a spring 706 and a spring load washer 707. In the proximal end the tubular locking element 705 may be threadingly engaged on the outside with a locking knob 708. In the distal end of the tubular locking element 705, the locking element 705 may be threadingly engaged with a locking unit 709. The locking unit 709 comprises distal locking tongues 710, forming a female mating connection, which may be radially compressed within the top connector 703, when they move proximally from d1 to d2. The locking tongues 710 may have inner flanges. Thereby, a corresponding male mating connection, placed within the tongues 710, may be fixed from distal movement when the locking unit 709, and thereby the tongues 710 are moved proximally within the top connector 703 from d1 to d2. Since the fixation element 701 is a tubular element, a lumen or central passage through the fixation element is present.

When the first part has been inserted through the sphincter of the patient with a preloaded flexible part of an anastomotic device arranged on the shelf 401, while the elongated tubular sheet element 101 and the cutting element 301 are in a spring loaded position, the flexible part of the anastomotic device positioned on the shelf 401 is ready to be arranged on a rigid part of an anastomotic device.

Once the first part 100 is positioned such that the receiving portion 104 is in close proximity of the end of the intestine onto which the flexible part of the anastomotic device is to be arranged, a suction device connected to the central passage may be turned on. When the suction device is turned on, the end of the intestine will be sucked into the central passage. Normally, the incisioned intestine is sutured or stitched at the cut end, to form a "blind" intestine, i.e. a cavity from the sphincter to the sutures or stitches. When the end of the intestine is sucked into the central passage, it will enclose the flexible part of the anastomotic device positioned on the shelf 401. It is also possible to omit the suction, and only insert the first part 100 to the bottom of the "blind" intestine. Thereafter, a second part 800, according to FIG. 8, may be arranged to cooperate with the first part 100, to clamp the intestine therebetween and position a rigid part of an anastomotic device adjacent the intestine and the flexible part of the anastomotic device.

Figure 8:
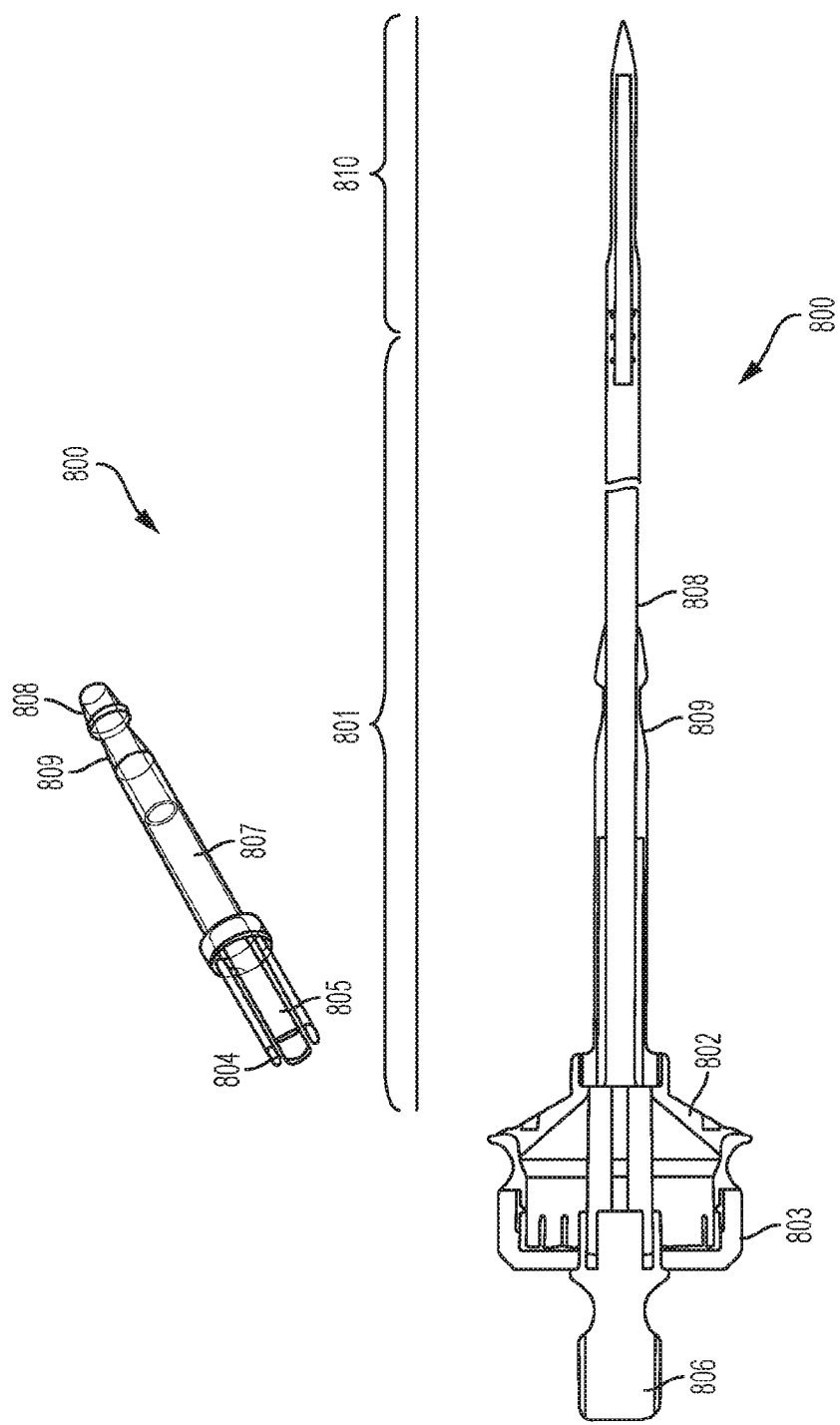
FIG. 8 illustrates a cross section of an embodiment of a second part of a mounting tool according to the present invention.

The second part 800 according to the embodiment illustrated in FIG. 8, comprises a longitudinal guiding element 801. The guiding element 801 may be of a hollow configuration. When the guiding element 801 is of a hollow configuration it may house catheters connected to rigid part of an anastomotic device. In the distal end of the second part 800 a connection plate 802 is positioned. The connection plate 802 is configured to be snap-in fitted or screw fitted with a rigid part of an anastomotic device in the distal end thereof. The rigid part of an anastomotic device may also be seated on the distal part of the connection plate 802, whereafter the rigid part of the anastomotic device is clamped in-between the connection plate and a hood 803. Simultaneously, the proximal end of the connection plate may be configured to closingly fit and/or attach to the receiving portion 104 of the first part 100, such that the distal end 204 of the displacement element 201 cooperates with the proximal end of the connection plate 802. In this respect the proximal end of the connection plate 802 may be substantially conical towards the connection with the guiding element 801. The guiding element 801 may extend through the connection plate 802, such that it also will pass through a rigid part of an anastomotic device connected to the distal part of the connection plate 802, if the risk of too early disengagement between the connection plate 802 and the rigid part is to be reduced. In the event the second part 800 is to be used in connection with a rigid part of an anastomotic device bearing catheters, the part extending distally through the connection plate 802 may be provided with through slots 804, such that tongues 805 are created therebetween. The catheters connected to the rigid part of an anastomotic device may the extend radially outwards through said through slots and connect to the rigid part of the anastomotic device. When the connection plate 802 is liberated from the rigid part of an anastomotic device bearing catheters, the catheters may slide along the tongues 805 out through the mouth of the through slots 804. Distally of the rigid part of an anastomotic device the hood 803 may be attached to the guiding element 801 and/or the tongues 805, if the risk of too early disengagement between the rigid part and the connection plate 802 is to be reduced. The hood 803 may be a disc shaped unit with a diameter at least corresponding with the distal diameter of a rigid part of an anastomotic device, whereby it may maintain the rigid part on the second part. The connection between the hood 803 and the guiding element 801 and/or the tongues 805 may be accomplished by screw-fitting or snap-in fitting. The hood 803 may be a disc shaped unit with a central passage, allowing the guiding element 801 and/or the tongues 805 to pass there through and connect to a hood locker 806, positioned distally of the hood 803. The hood locker 806 may have male threading part corresponding to a female threading part on the inside of the guiding element 801 and/or the tongues 805. Distally of the guiding element 801 and proximally of the connection plate 802 a male locking unit 807 is arranged. The male locking unit 807 is configured to cooperatively mate with the female mating connection, formed by locking tongues 710, of the fixation element 701. In the proximal end the locking unit 807 comprises a cone shaped male member 808, having a recess 809 distally thereof, to enhance the fixation action between the fixation element 701 and the second part 800. In the proximal end of the second part 800 a tip portion 810 is provided, to facilitate the introduction of the second part 800 through the first part 100. The tip portion 810 may be provided as a spike to facilitate penetration of the intestine, in case the intestine has been sutured or stitched into a "blind" intestine.

The tip portion 810 may then be inserted in the central lumen of the first part 100, i.e. the central lumen of the tubular locking element 705. The tip portion 810 may then pass through the first part 100, exiting the locking knob 708 in the proximal end of the first part 100. Then the tip portion 810 is pulled proximally, such that the cone shaped male member 808 enters the female mating connection, formed by locking tongues 710. The flanges of the tongues 710 may then snap-fit with the recess 809 distal of the male member 808. Thereafter, the locking knob 708 is tightened, such that the locking unit 709 is pulled proximally from d1 to d2, thus locking the locking unit 807 to the fixation element 701. By further tightening of the locking knob 708 the second part 800 is pulled and centralized through/in the first part 100, until the connection plate 802 squeezes the intestine against the displacement element 201. In this position the spring bars 107 may be pushed inwardly to release the spring 106, whereby relative movement between the sheet element 101 and the displacement element 201 is accomplished to push the flexible part 402 off the shelf 401, as disclosed above.

According to one embodiment a central hollow guide may pass through the connection plate 802 and the rigid part of an anastomotic device to distally connect to the hood 803 or hood locker 806.

Thus, the second part 800 is arranged to cooperate with the first part by inserting the guiding element 801 in the distal opening of the first part, and passing the guiding element 801 through the first part to exit in the handle portion.

Alternatively, the guiding element 801 is configured to substantially correspond to the length of the first part, such that it may be screw connected to the handle of the first part 100. Thereafter, the intestine may be squeezed in between the displacement element 201 and the connection plate 802. Thus, the proximal end of the guiding element 801 may be provided with a male thread mating with a female thread on the first part, such as on the handle portion.

Figure 9:
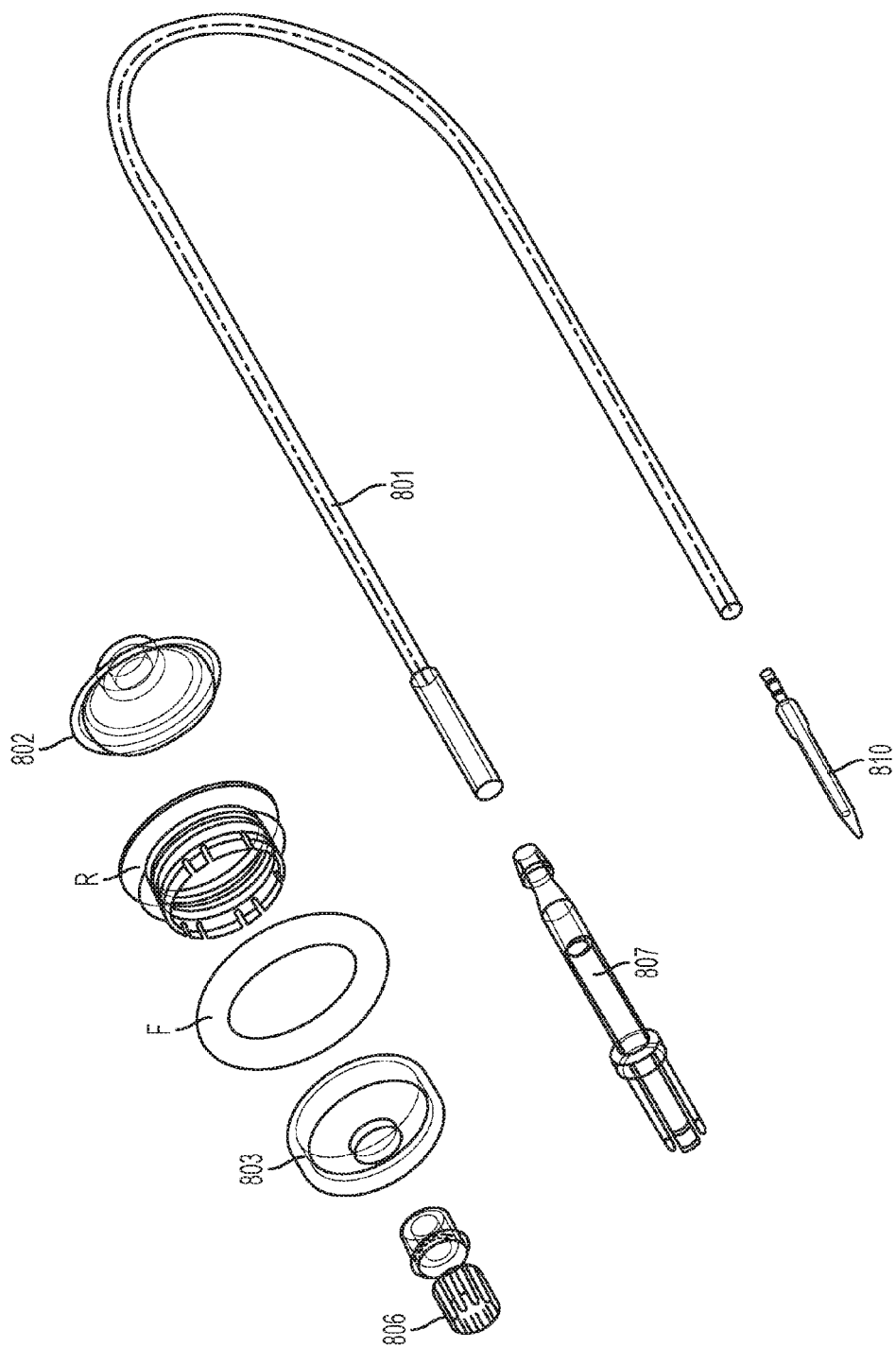
FIG. 9 illustrates an exploded view of an embodiment of a second part of a mounting tool according to the present invention.

FIG. 9 illustrates an exploded view of the arrangement of a flexible part of an anastomosis device F and a rigid part of an anastomosis device R on the second part 800.

Figure 10:
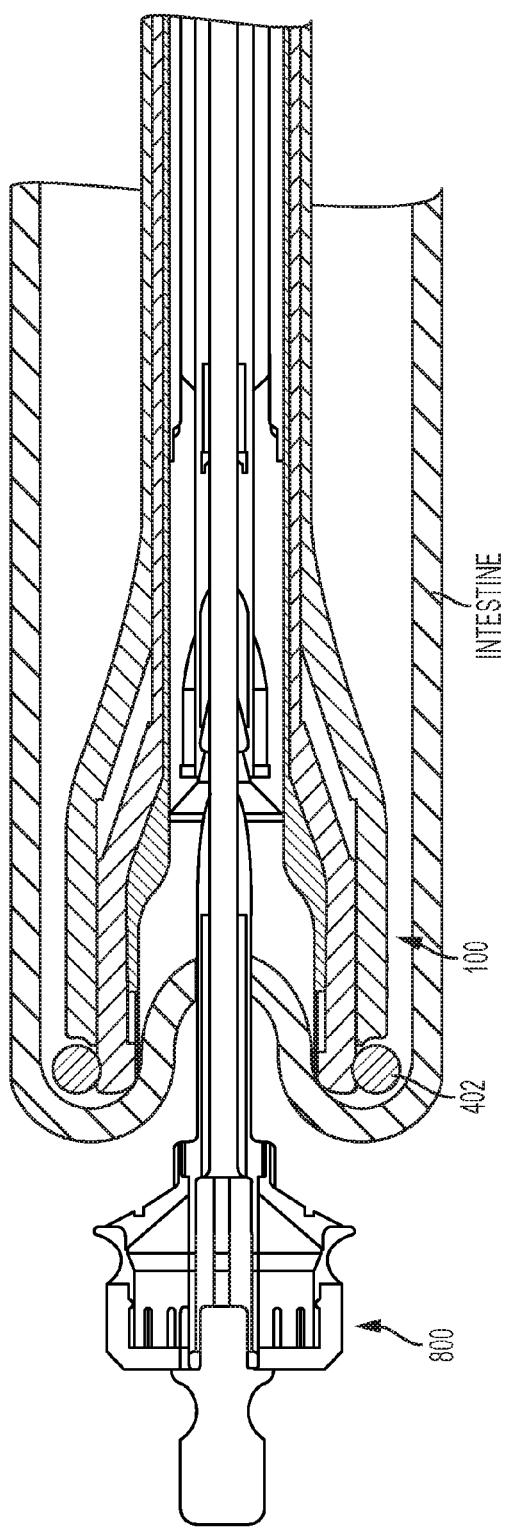
FIG. 10 illustrates a cross section of an embodiment of an intestine, a first part, and a second part of a mounting tool according to the present invention.

FIG. 10 illustrates a first part 100 arranged inside an intestine I, according to the disclosure above. The intestine I has been sutured or stitched into a "blind" intestine, in accordance with disclosure above. A second part 800 has been arranged through the intestine I, such that a flexible part 402 of an anstomotic device is arranged at the distal end thereof.

When the intestine is squeezed between the displacement element and the connection plate, the first release bars 107 of the first part 100 may be activated to activate relative movement between the sheet element 101 and the displacement element 201, such that distal movement of the sheet element 101 with respect to the displacement element 201 is obtained. When the sheet element 101 moves distally with respect of the displacement element 201, the flexible part of the anastomotic device is pushed off the shelf onto the rigid part of the anastomotic device. This is disclosed in FIG. 11.

Figure 11:
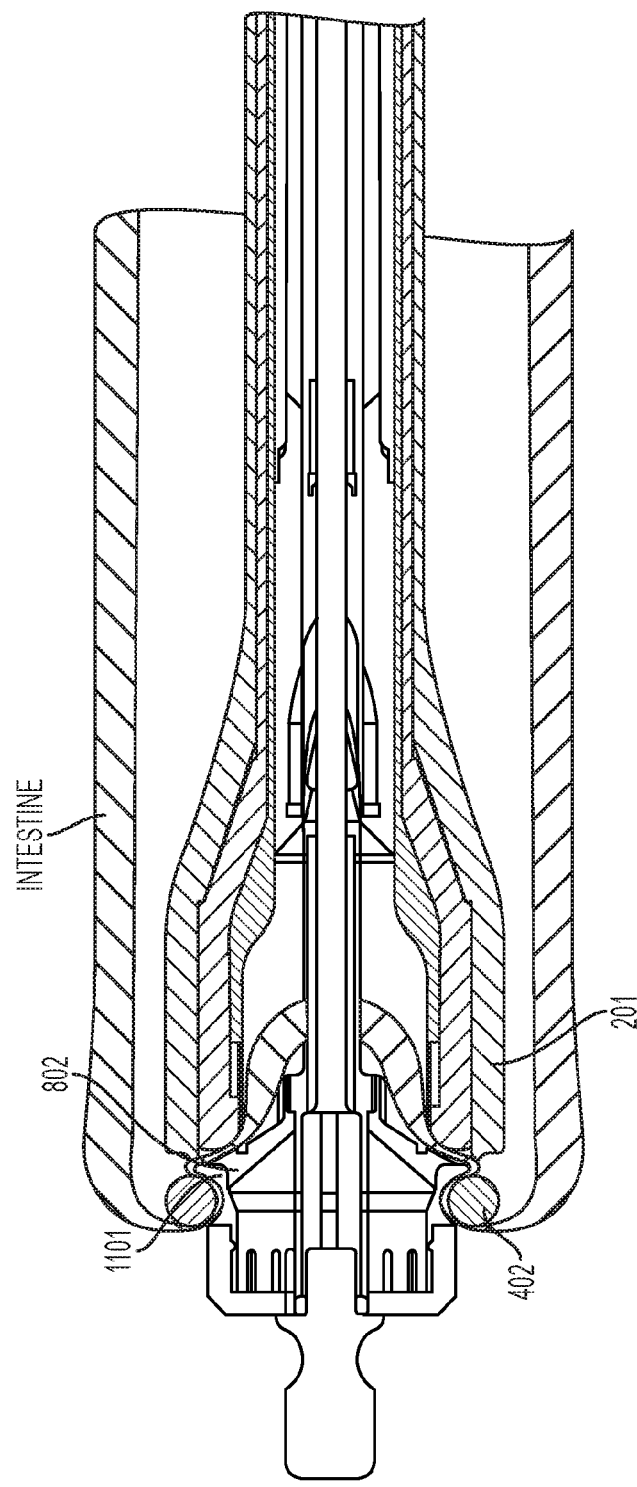
FIG. 11 illustrates a cross section of an embodiment of an intestine, a first part, and a second part of a mounting tool according to the present invention.

FIG. 11 illustrates how the second part 800 has been fixed to the first part 100 by the cooperation of the fixation element 701 and the male member 808 of the second part 800. The intestine I is squeezed in-between the connection plate 802 and the displacement element 201. The first set of release bars 107 has been activated to push the flexible part 402 onto a rigid part 1101, in accordance with the disclosure above.

Then, the second release bars may be activated, whereafter the cutting element will move distally with regard to the displacement element to cut off the intestine radially inwards of the displacement element, when the cutting element hits the proximal surface of the conical connection plate. In this respect the conical proximal surface of the connection plate may have a suitable hardness. A suitable hardness may be a hardness in the interval of 70 to 100 shore, and preferably 85 to 95 shore.

Figure 12:
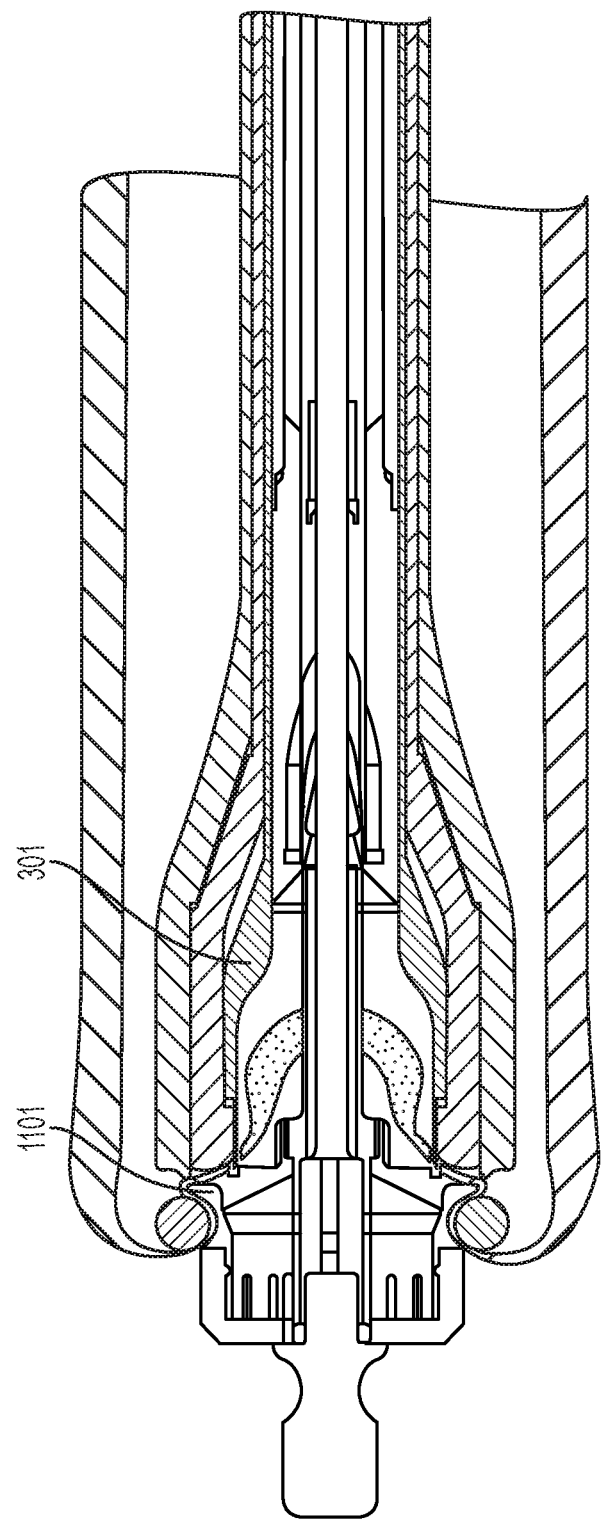
FIG. 12 illustrates a cross section of an embodiment of an intestine, a first part, and a second part of a mounting tool according to the present invention.

FIG. 12 illustrates how, the second set of release bars 207 has been activated to move the cutting element 301 distally with respect to the sheet element 101 and the displacement element 201, in accordance with the disclosure above, such that the intestine I is cut to create a hole substantially corresponding to the lumen of the rigid part 1101 of the anastomotic device.

Thereafter—when a hood is placed distally of the rigid part—the hood 803 may be released from the guiding element 801 by disengaging the hood locker 806 from the guiding element 801, the tongues 805, or the central wire, by releasing the snap fit or the screw fit therebetween.

When the hood 803 has been removed, the rigid part of the anastomotic device—now with the intestine squeezed between the rigid part and the flexible part of the anastomotic device—may be connected to another rigid part, bearing a flexible part thereon, with the other end of the intestine squeezed therebetween. Said other rigid part may for example be assembled to the other end of the intestine by the aid of a mounting tool disclosed in the international patent application with publication number WO 2007/122220.

When the two rigid parts of the anastomotic device has been connected, the first part 100 and the second part 800 are released from the rigid part of the anastomotic device by disconnecting the rigid part from the connection plate and loosing the pressure between the proximal conical surface of the connection plate and the displacement element. This may be accomplished by releasing the screw or snap-in fit between the connection plate and the rigid part, and releasing the screw fit between the guiding element and the first part.

The elements and components of an embodiment of the invention may be physically, functionally and logically implemented in any suitable way. Indeed, the functionality may be implemented in a single unit, in a plurality of units or as part of other functional units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. An anastomotic device comprising:
a mounting tool;
a flexible ring-shaped part; and
a rigid part;
wherein the flexible ring-shaped part is configured to be mounted on the rigid part;
the mounting tool including:
a receiving portion at a distal end of the mounting tool for receiving the flexible ring-shaped part thereat; and
a handle portion proximal of the receiving portion;
wherein the receiving portion includes:
a tubular sheet element,
a tubular displacement element arranged within the tubular sheet element, the tubular displacement element being longitudinally displaceable relative to the tubular sheet element, such that a shelf is obtained circumferentially of the tubular displacement element and distally of the tubular sheet element, the shelf being configured to receive the flexible ring shaped part, and
a tubular cutting element inside the tubular displacement element, such that the tubular cutting element is longitudinally displaceable within and in relation to the tubular displacement element;
wherein the tubular cutting element is configured to deploy after:
the shelf has been withdrawn into the tubular sheet element, and
a distal end of the tubular displacement element has been pressed against a proximal end of the rigid part of the anastomotic device; and
wherein a release of a spring load proximal of the receiving portion will impart a relative movement between the tubular sheet element and the tubular displacement element.

2. The anastomotic device according to claim 1, wherein a central portion connects the handle portion and the receiving portion, and
wherein the central portion has an outer diameter that is smaller than an outer diameter of at least one of the handle portion and the receiving portion.

3. The anastomotic device according to claim 1, wherein the tubular sheet element and the tubular displacement element have ring-shaped cross sections, and
wherein an outer diameter of the tubular displacement element substantially corresponds to an inner diameter of the tubular sheet element, such that the tubular displacement element may run longitudinally inside the tubular sheet element.

4. The anastomotic device according to claim 1, wherein the tubular cutting element has a ring-shaped cross section, and
wherein an outer diameter of the tubular cutting element substantially corresponds to an inner diameter of the tubular displacement element.

5. The anastomotic device according to claim 1, comprising:
at least one of a first set of release bars and a second set of release bars, corresponding to the tubular sheet element and the tubular cutting element, respectively, releasing the spring load when activated.

6. The anastomotic device according to claim 5, wherein the first set of release bars have a supporting ridge;
wherein the distal end of the supporting ridge is provided with an inwardly directed flange; and
wherein the inwardly directed flange, in a spring loaded position, engages a notch in the tubular displacement element.

7. The anastomotic device, according to claim 5, wherein the second set of release bars have a supporting ridge;
wherein the second set of release bars are connected to the supporting ridge by a tongue and the proximal end of the tongue is provided with an inwardly directed flange; and
wherein the flange, in a spring loaded position, engages a notch in the tubular cutting element.

8. The anastomotic device according to claim 1, comprising:
a central passage for connection to a suction device in the proximal end of the mounting tool.

9. The anastomotic device according to claim 1, comprising:
a tubular fixation element including
a tubular connector element, the tubular connector element in the distal end thereof having a tubular top connector, and in the proximal end thereof being connected to a connector unit, and
a tubular locking element inside the tubular connector element, the tubular locking element being displaceable therein, the tubular locking element, in the distal end thereof, having a locking unit.

10. The anastomotic device according to claim 9, wherein the locking unit includes distal locking tongues with inner flanges, forming a female mating connection, which may be radially compressed within the tubular top connector, when they move proximally.

11. The anastomotic device according to claim 8, comprising:

a longitudinal guiding element for passing through the central passage; and a connection plate arranged distally on the longitudinal guiding element, the connection plate being configured to connect to the rigid part of the anastomotic device.

12. The anastomotic device according to claim 11, wherein the guiding element has a hollow configuration.

13. The anastomotic device according to claim 11, wherein the connection plate has a substantially conical shape, with a proximal top end and a distal base end, and is configured to be snap-in fitted or screw fitted circumferentially with the rigid part of the anastomotic device in the distal end thereof.

14. The anastomotic device according to claim 11, wherein a proximal conical surface of the connection plate is configured to at least one of closingly fit and attach to the receiving portion of the mounting tool.

15. The anastomotic device according to claim 11, wherein the longitudinal guiding element extends through the connection plate, such that it also will pass through the rigid part of the anastomotic device connected to the distal part of the connection plate.

16. The anastomotic device according to claim 15, wherein a part of the longitudinal guiding element extending distally through the connection plate is provided with through slots, such that tongues are created therebetween.

17. The anastomotic device according to claim 11, comprising:
a hood releasably connected to the longitudinal guiding element distally of the rigid part of the anastomotic device attached to the connection plate.

18. The anastomotic device according to claim 17, wherein the hood is a disc shaped unit with a central passage.

19. The anastomotic device according to claim 18, wherein the longitudinal guiding element extends through the central passage of the hood and connects to a hood locker, which is positioned distally of the hood.

20. A kit comprising:
a) an anastomotic device including:
a mounting tool;
a flexible ring-shaped part;
a rigid part;
wherein the flexible ring-shaped part is configured to be mounted on the rigid part;
the mounting tool including:
a receiving portion at a distal end of the mounting tool for receiving the flexible ring-shaped part thereat, and
a handle portion proximally of the receiving portion, wherein the receiving portion includes:
a tubular sheet element,
a tubular displacement element arranged within the tubular sheet element, the tubular displacement element being longitudinally displaceable relative to the tubular sheet element, such that a shelf is obtained circumferentially of the tubular displacement element and distally of the tubular sheet element, the shelf being configured to receive the flexible ring shaped part, and
a tubular cutting element inside the tubular displacement element, such that the tubular cutting element is longitudinally displaceable within and in relation to the tubular displacement element;
wherein the tubular cutting element is configured to deploy after:
the shelf has been withdrawn into the tubular sheet element, and
a distal end of the tubular displacement element has been pressed against a proximal end of the rigid part of the anastomotic device,
wherein a release of a spring load proximal of the receiving portion will impart a relative movement between the tubular sheet element and the tubular displacement element; and
b) a tubular fixation element including:
a tubular connector element, the tubular connector element in the distal end thereof having a tubular top connector, and in the proximal end thereof being connected to a connector unit, and
a tubular locking element inside the tubular connector element, the tubular locking element being displaceable therein, the tubular locking element, in the distal end thereof, having a locking unit.

* * * * *